United States Patent [19]

Ohmori et al.

[11] Patent Number: 5,515,131
[45] Date of Patent: May 7, 1996

[54] OPTICAL APPARATUS HAVING A FUNCTION OF INPUTTING DATA OF A VISUAL AXIS

[75] Inventors: Koichi Ohmori, Yokosuka; Kenji Suzuki, Kawasaki, both of Japan

[73] Assignee: Canon Kabushiki Kaisha, Tokyo, Japan

[21] Appl. No.: 357,137

[22] Filed: Dec. 15, 1994

Related U.S. Application Data

[63] Continuation of Ser. No. 108,912, Aug. 17, 1993, abandoned.

[30] Foreign Application Priority Data

Aug. 24, 1992 [JP] Japan ..................... 4-246040

[51] Int. Cl.⁶ ................................... G03B 17/20
[52] U.S. Cl. ........................................... 354/410
[58] Field of Search ..................... 354/400, 402, 354/410, 432, 219, 62

[56] References Cited

U.S. PATENT DOCUMENTS 3,936,849  2/1975  Tsujimoto ..................... 354/195
5,214,466  5/1993  Nagano et al. .................. 354/402
5,245,381  9/1993  Takagi et al. ................. 354/219 X
5,253,008  10/1993 Konishi et al. .................. 354/402

FOREIGN PATENT DOCUMENTS

0055338A1  7/1982  European Pat. Off. .
1-241511   9/1989  Japan .
2117594   10/1983 United Kingdom .

Primary Examiner—W. B. Perkey
Attorney, Agent, or Firm—Fitzpatrick, Cella, Harper & Scinto

[57] ABSTRACT

An apparatus having a constitution for detecting directions of the user's visual axis and exhibiting desirable functions of the apparatus according to detected data, and a constitution for judging output from an object sensor according to predetermined algorithm and exhibiting functions of the apparatus according to the result of judgement, wherein proper operations are performed even when detection of the visual axis directions is forbidden.

29 Claims, 10 Drawing Sheets

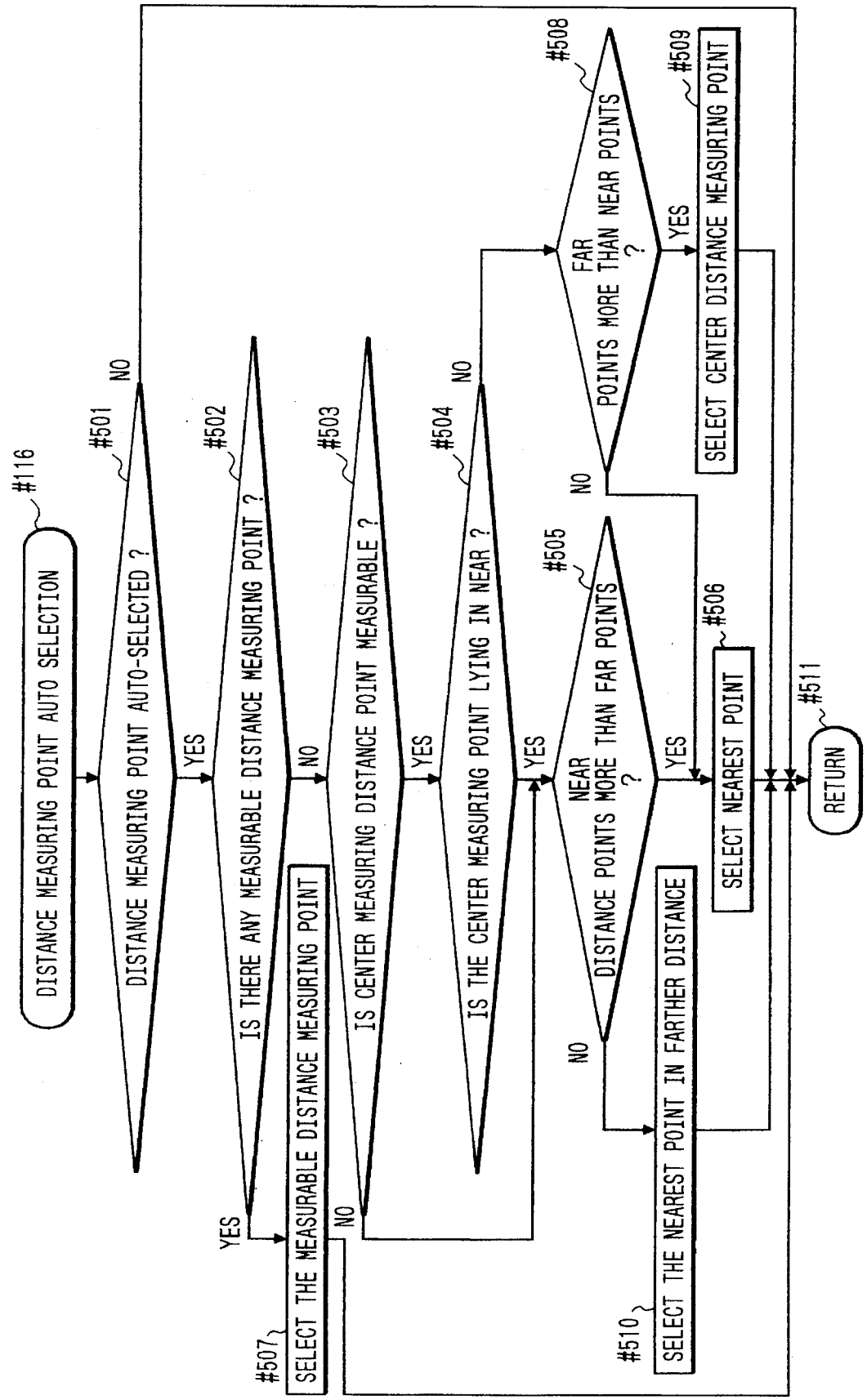

OPTICAL APPARATUS HAVING A FUNCTION OF INPUTTING DATA OF A VISUAL AXIS

This application is a continuation of application Ser. No. 08/108,912 filed Aug. 17, 1993, now abandoned.

BACKGROUND OF THE INVENTION

1. Field of the Invention

The present invention relates to improvement on an optical apparatus having a function of detecting a visual axis which is provided with a visual axis detecting means for detecting a rotation angle of an optical axis of an eyeball of the user who looks a field of view in a finder as well as detecting the visual axis of the user on the basis of said detected rotation angle.

2. Related Background Art

Various kinds of optical apparatus for detecting which position in an observed area an observer observes; that is, detecting a visual axis (or a stared point) have been proposed, including an eye camera and a photographing apparatus which is disclosed in Japanese Patent Appln. Laid-Open No. 1-241511. For example, in Japanese Patent Appln. No. 4-167014 there is disclosed an optical apparatus which has a visual axis detecting means as a part of a finder system and performs various kinds of photographing operation by utilizing data of a visual axis obtained by said visual axis detecting means.

In this kind of apparatus, it is very difficult to simplify the entire apparatus and, at the same time, to detect the visual axis of the photographer who looks into the field of view in a finder with high precision in order to perform photographing operation. For example, if the photographer wears glasses having high surface reflectance, a ghost image caused by reflected light from the glasses reduces precision of detection. Also, if the eyeball is illuminated with a light beam from an highly luminous object (a light source, the sun, and so on) in the field of view in a finder, the reflected light beam from the eyeball reduces precision of detection.

Accordingly, when various kinds of photographing operation are performed on the basis of visual axis data by the above-mentioned camera having the visual axis detecting means, data of the visual axis may be inexact, and sometimes, data can not be obtained at all. In this case, the photographing operation is not performed according to the wishes of the photographer and desired images can not be obtained.

SUMMARY OF THE INVENTION

An object of the present invention is to provide an apparatus which operates properly even when detection of a visual axis direction is forbidden, wherein said apparatus is provided with structure in which the user's visual axis direction is detected and desired functions of the apparatus are exhibited according to detected data, as well as with structure in which output from an object sensor is judged according to predetermined algorithm and functions of the apparatus are exhibited according to results of judgement.

Another object of the present invention is to provide an optical apparatus having a visual axis detecting function which can always obtain images according to the wishes of the user, wherein use of an eye-control mode for performing photographing operation according to visual axis data can be restricted and an eye-control forbidding mode capable of performing photographing operation without using said visual axis data can be properly selected.

Still another object of the present invention is to provide a photographing apparatus comprising: a visual axis detecting means for detecting the rotation angle of the eye ball of the user who looks into the field of view in a finder and detecting the visual axis of the user on the basis of said rotation angle; a control means for controlling a photographing functions according to the visual axis data from said visual axis detecting means in the eye-control mode and controlling the photographing functions without using the visual axis data from said visual axis detecting means in the eye-control forbidding mode; and a selection means for selecting the eye-control mode or the eye-control forbidding mode according to setting of the photographing mode, wherein either said eye-control mode or said eye-control forbidding mode is uniquely selected.

BRIEF DESCRIPTION OF THE DRAWINGS

FIG. 10 is a flowchart showing the operation of "distance measuring point auto-selection" in FIG. 7.

DETAILED DESCRIPTION OF THE PREFERRED EMBODIMENT

Figure 1:
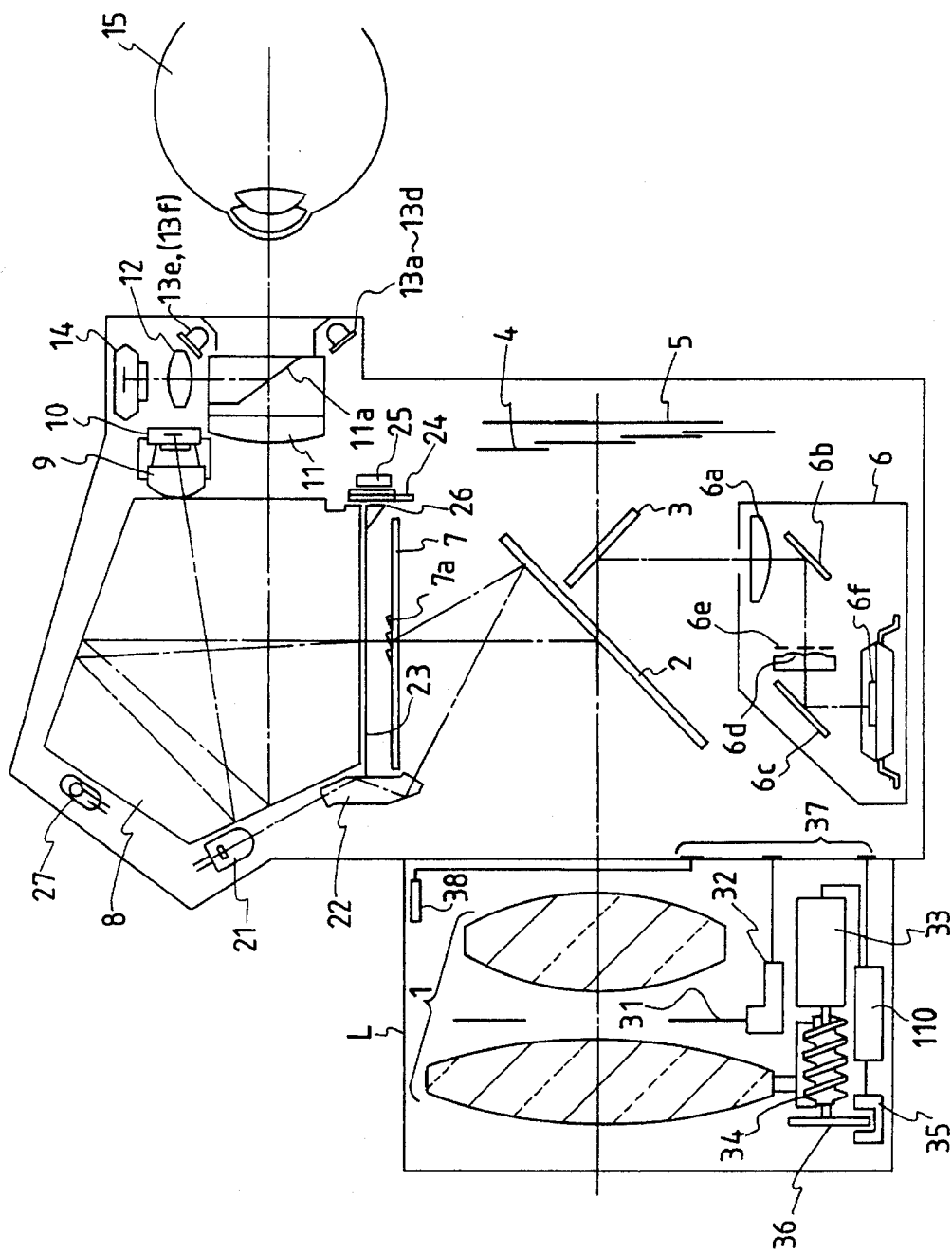
FIG. 1 is a view showing the major components of the first embodiment of the present invention, which is applied to a single-lens reflex camera.

The present invention will be described below in detail with reference to an embodiment shown in the drawings.

Figure 2A:
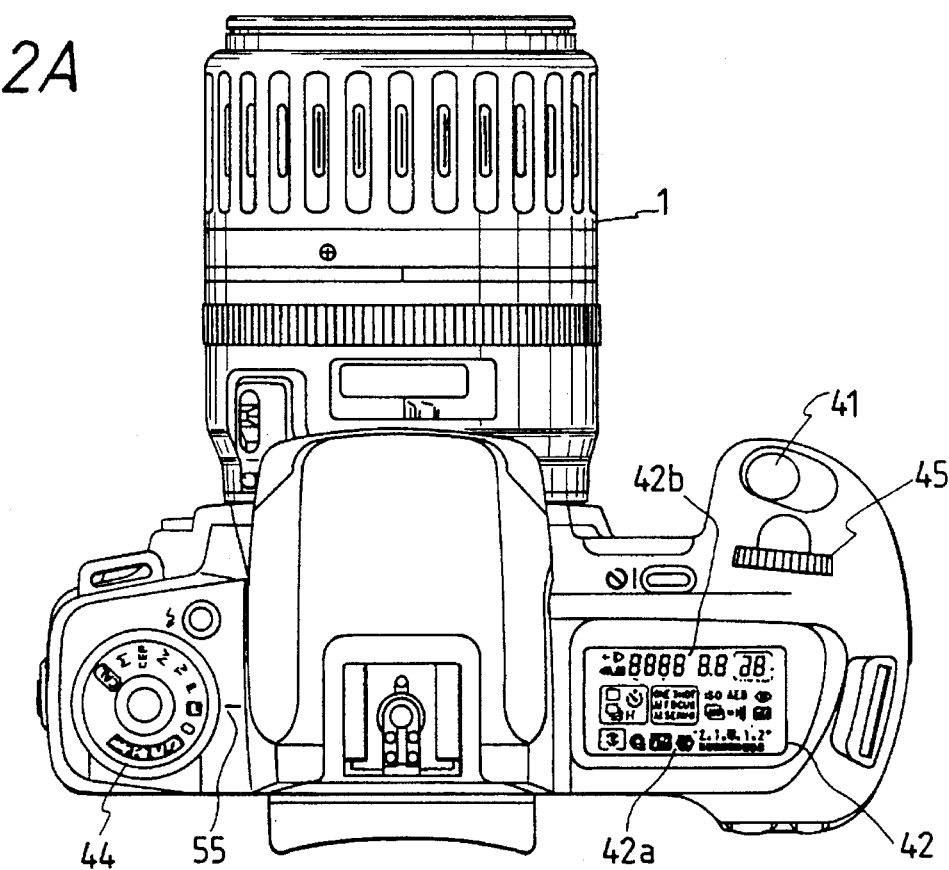
FIGS. 2A and 2B show the top view and the rear view of the single-lens reflex camera shown in FIG. 1, respectively.
Figure 2B:
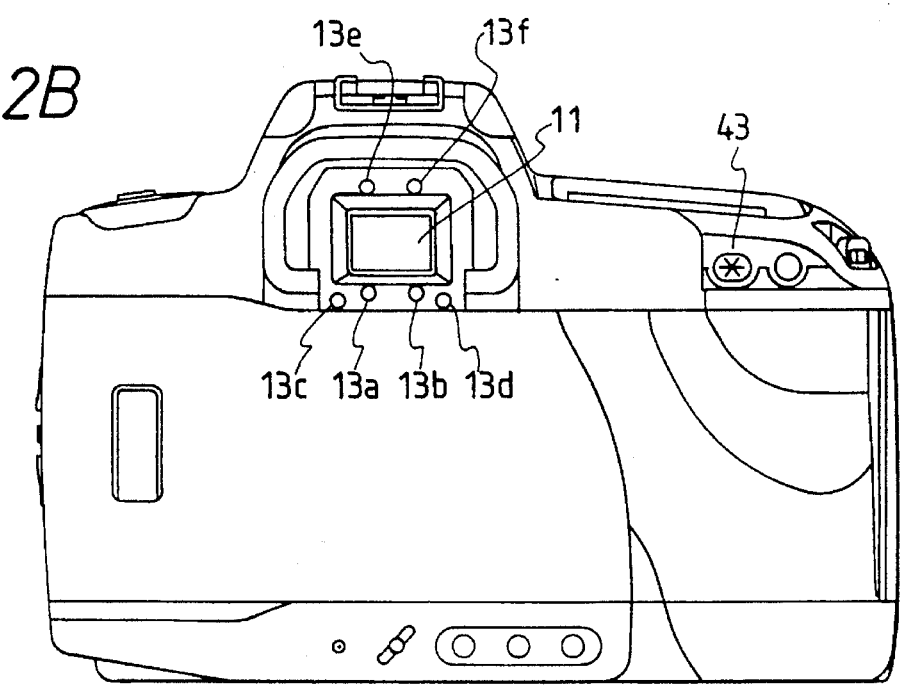
Figure 3:
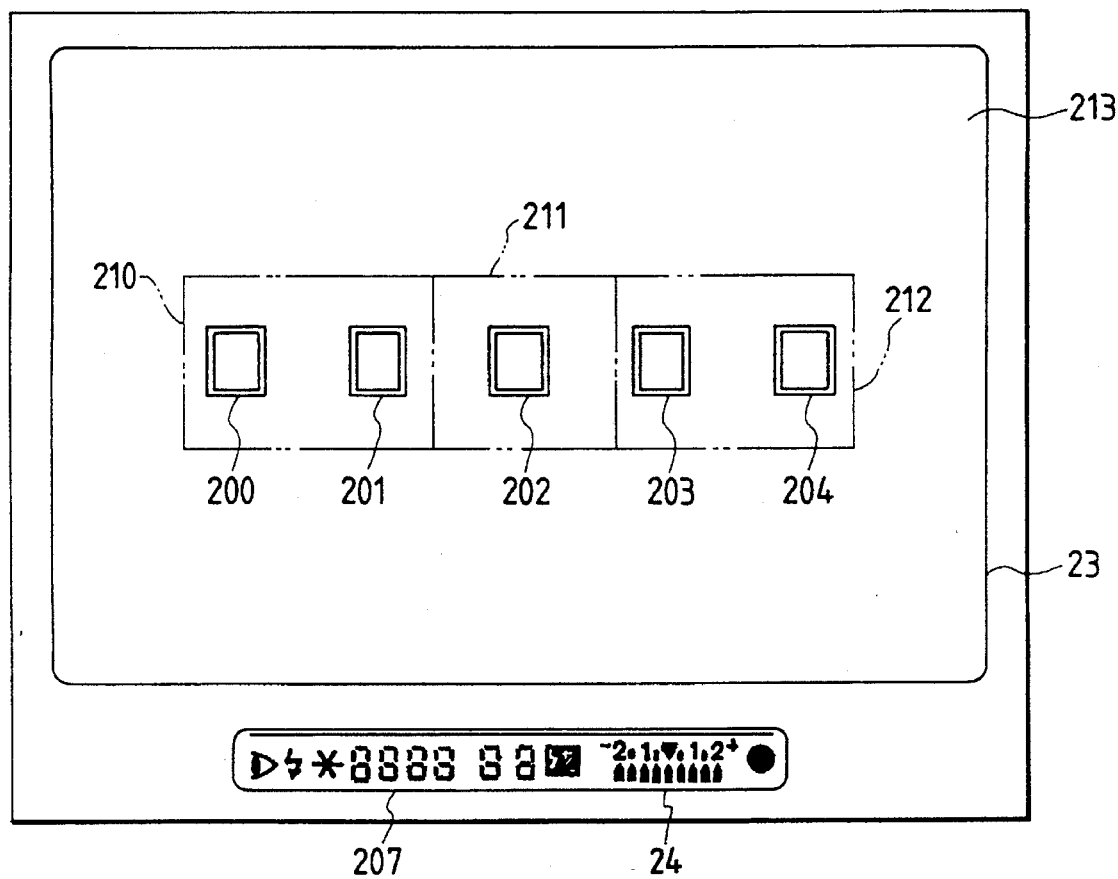
FIG. 3 is an explanatory plan view of the field of view in a finder.

FIG. 1 is a schematic view showing the major portions of the first embodiment, wherein the present invention is applied to a single-lens reflex camera. FIGS. 2A and 2B are a top view and a rear view of the same, respectively. FIG. 3 is an explanatory view of the field of view in a finder shown in FIG. 1.

In these figures, a photographing lens system L is either detachably mounted or fixedly provided to the camera main body. Though shown as two lenses for the sake of convenience, a lens system actually consists of more lenses. A main mirror 2 is slanted or retreated with respect to an image pick-up light path with correspondence to the conditions of the object image observed through a finder system and the photographing conditions of the object. A sub-mirror 3 reflects the light beam transmitted through the main mirror 2 toward a focal point detecting device 6 (described later) at the bottom of the camera body.

Reference numeral 4 indicates shutters, and a photosensitive member 5 is a silver salt film, a solid image pick-up element such as a CCD and an MOS, and a camera tube such as a vidicon.

A focal point detecting device 6 comprises: a field lens 6a arranged in the vicinity of an image forming surface; reflecting mirrors 6b and 6c; secondary image forming lens array 6d; multi diaphragm 6e; a line sensor 6f consisting of a plurality of CCD, and so on.

In this embodiment, the focal point detecting device 6 performs focal point detection by the well known phase difference method, wherein, as shown in FIG. 3, a plurality of regions (that is, five points 200 to 204) are defined as distance measuring points in the observed area (in the field of view in a finder), and focal points of the object corresponding to respective distance measuring points can be detected.

A focus plate 7 is arranged in an estimated image forming surface of the photographing lenses 1, and a pentagonal prism 8 is provided to bend the finder light path. An image forming lens 9 and a photometry sensor 10 are provided to measure luminance of the object in the observed area. By means of the image forming lens 9, the focus plate 7 and the photometry sensor 10 are located, through the reflected light path in the pentagonal prism 8, at the conjugate positions with respect to each other.

Further, an eyepiece 11 having a light separating device 11a is provided behind the emission surface of the pentagonal prism 8 so as to be used for observation of the focus plate 7 by the eye 15 of the photographer. The light separating device 11 is, for example, a dichroic mirror which transmits visible light while reflects infrared rays. Incidentally, the eyepiece may be arranged on the photographer side.

A light receiving lens 12 is used for forming images. An image sensor 14 consists of arrays of photoelectric transfer elements such as CCD arranged two-dimensionally, and is arranged at the conjugate position with respect to the vicinity of the pupil of the photographer's eye 15 which is at a predetermined position with respect to the light receiving lens 12. Infrared light emitting diodes 13a to 13f serving as illumination light sources are arranged around the eyepiece 11 as shown in FIG. 2B.

LEDs for superimposition 21 having high luminance can be visible even against a bright object. Light emitted from the LED for superimposition 21 passes through a light projecting prism 22, is reflected by the main mirror 2 and is bent orthogonally by micro prism arrays 7a provided in the display unit of the focus plate 7, and finally, through the eyepiece 11, reaches the photographer's eye 15. Five LEDs for superimposition are aligned in the vertical direction to the drawing (page space) and are turned on independent of one another.

Said micro prism arrays 7a are formed in the shape of a frame at the plurality of distance measuring points corresponding to respective focal point detection regions in the focus plate 7. These micro prism arrays 7a are illuminated with five corresponding LEDs 21 for superimposition (that is, LED-L1, LED-L2, LED-C, LED-R1 and LED-R2 in FIG. 5).

Accordingly, respective distance measuring point marks 200, 201, 202, 203 and 204 shine in the field of view in a finder shown in FIG. 3 to display the focal point detecting regions (distance measuring points) (such display is hereinafter referred as "super-imposition display").

A field mask 23 forms the area of field of view in a finder, and a liquid crystal device (LCD) 24 in the finder displays photographing data outside the finder area, and is illuminated by an LED for illumination 25 (F-LED).

The light transmitted through the LCD 24 in the finder is led into the field of view in a finder by a triangular prism 26 to be displayed outside the finder area as indicated by reference numeral 207 in FIG. 3 so that the photographer is informed of the photographing information. Reference numeral 27 denotes a well known mercury switch for detecting the angle (whether vertical or horizontal) of the camera.

An aperture 31 is provided in the lens system L. An aperture driving device 32 includes an aperture driving circuit 111 (described later). Reference numeral 33 denotes a lens drive motor 33, and reference numeral 34 denotes a lens drive member including a driving gear and so on. A photo coupler 35 detects rotation of a pulse plate 36 working with said lens drive member 34, and informs a lens focal point control circuit 110 of detected rotation. The focal point control circuit 110 drives said lens drive motor 33 by a predetermined amount according to said information of detected rotation and that of the shifting amount of the lenses sent from the camera side, thereby shifting the lens system L into focus.

Reference numeral 37 denotes well known mount contact points serving as interfaces between the camera and the lenses. A switch 38 provided to the lenses selects whether the lens drive motor 33 is driven on the basis of the information of the shifting amount of the lenses from the camera or the focus lenses are driven manually.

In FIGS. 2A and 2B, reference numeral 41 denotes a release button, and a liquid crystal display unit (LCD) 42 for monitor, serving as an apparatus for external monitor display, consists of a fixed segment display unit 42a for displaying predetermined patterns and a seven-segment display unit 42b for displaying variable values. An AE lock button 43 is used to preserve photometric values, and a mode dial is for selecting photographing modes and so on. Other operating members are not described here, for the present invention is not directly concerned with them.

Figure 4A:
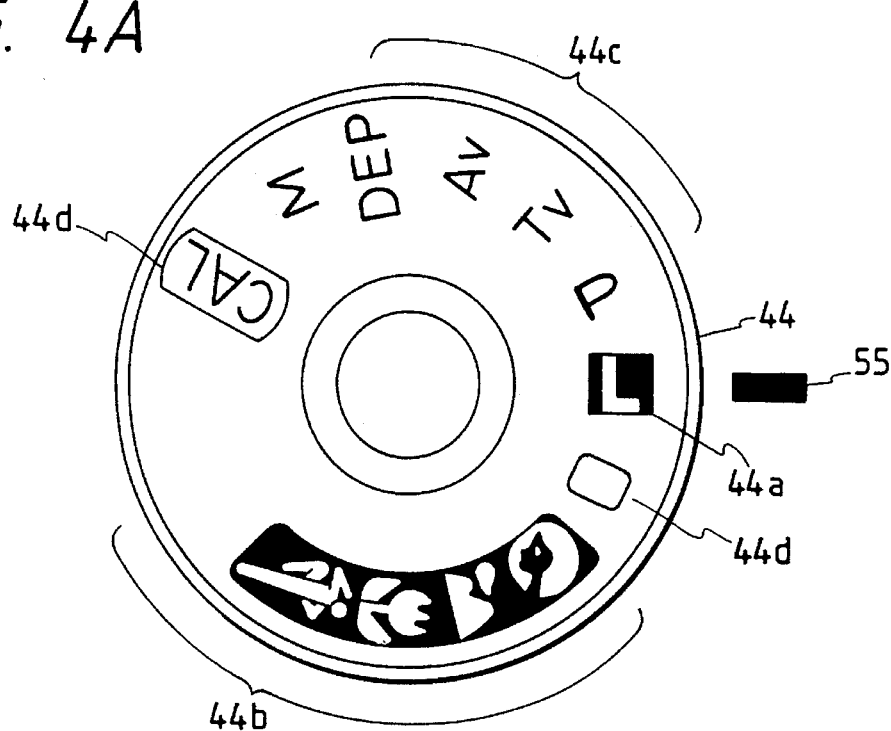
FIGS. 4A and 4B are explanatory plan views of the mode dial shown in FIG. 2A.
Figure 4B:
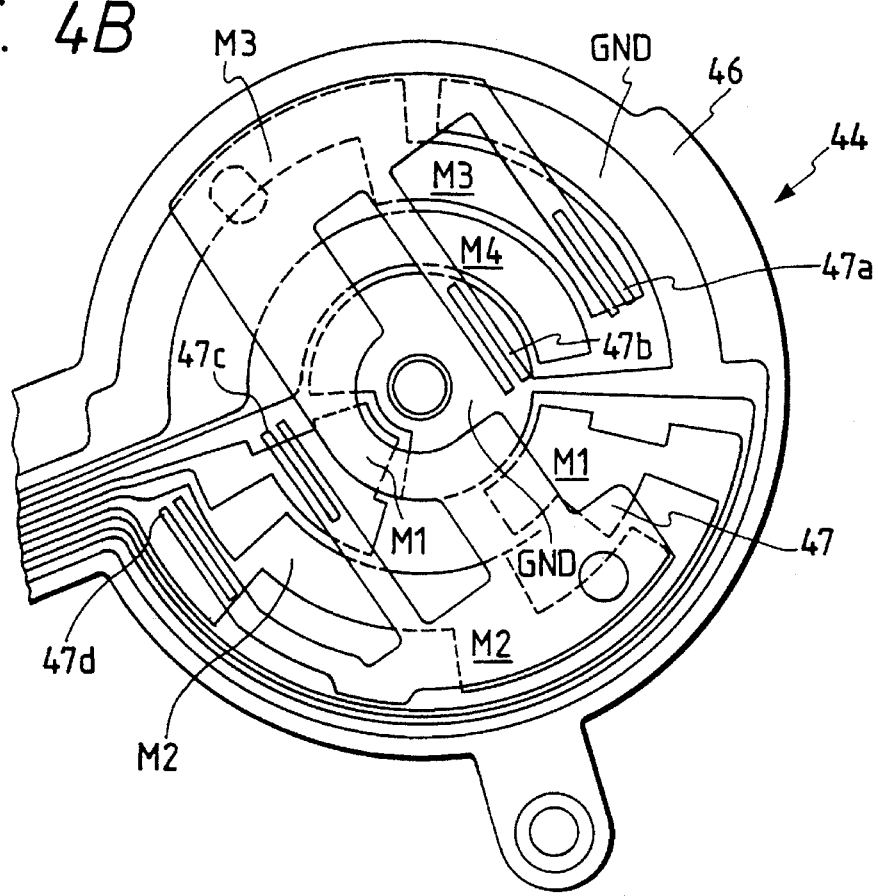

FIGS. 4A and 4B are views showing the constitution of the above-mentioned mode dial 44, wherein a photographing mode which is indicated by an index 55 printed on the camera main body by turning the mode dial is selected to be set.

In FIG. 4A, a lock position 44a is for making the camera inoperative; an auto photographing mode position 44b is for controlling the camera according to a predetermined photographing program; a manual photographing mode position 44c for permitting the photographer to select and set one of a plurality of photographing modes, that is, program AE, shutter precedence AE, diaphragm precedence AE, field depth precedence AE and manual exposure; and a full-auto photographing mode position 44d for automatically selecting and setting all the photographing modes.

FIG. 4B shows the internal constitution of the mode dial 44. On a flexible printed board 46, switch patterns (M1, M2, M3 and M4) serving as mode dial switches and a GND pattern are arranged as shown in the figure. By sliding four armatures (47a, 47b, 47c and 47d) constituting a switch armature 47 which is rotated together with the mode dial 44, twelve positions of the mode dial 44 can be set at four bits.

Let us return to FIGS. 2A and 2B, in which an electronic dial 45 rotates in a plane vertical to the page space and generates a click pulse so that a value in the mode selected by the mode dial 44 is further selected. For example, when the mode dial 44 selects the shutter precedence photographing mode, a currently set shutter speed is displayed in the LCD 24 in the finder and LCD 42 for monitor. As the photographer turns the electronic dial 45 in either direction, the shutter speed gradually varies, corresponding to said direction, from said currently set shutter speed.

Figure 5:
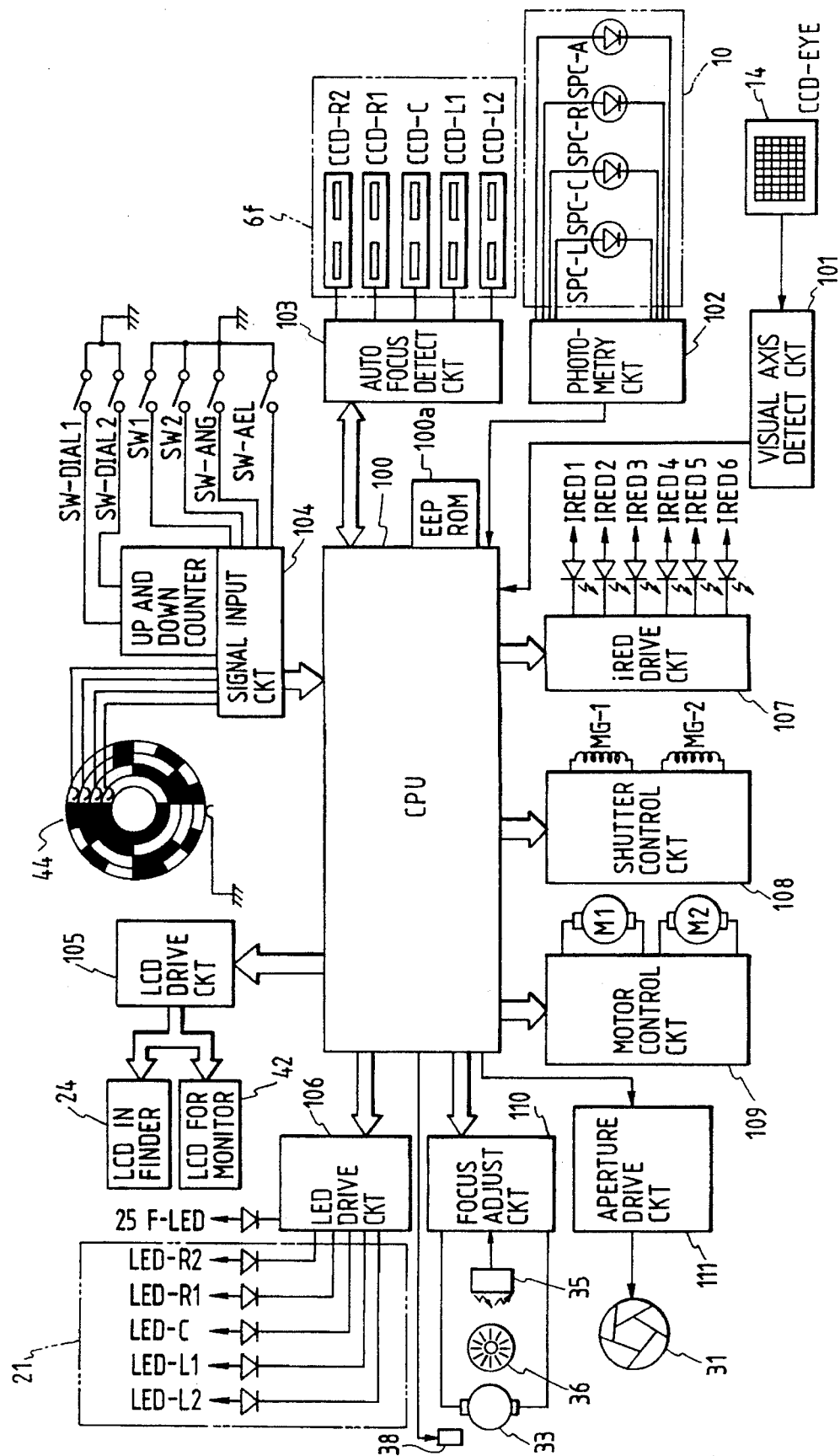
FIG. 5 is a block diagram showing the circuit constitution of the single-lens reflex camera shown in FIG. 1.

FIG. 5 is an explanatory view of the electric circuit contained in the single-lens reflex camera having the above-mentioned constitution.

A central processing unit (CPU) 100 of a micro computer contained in the camera main body is connected with: a visual axis detecting circuit 101; a photometry circuit 102; auto focal point detecting circuit 113; a signal input circuit 104; an LCD drive circuit 105; an LED drive circuit 106; an iRED drive circuit 107; a shutter control circuit 108; and a motor control circuit 109. And signals are transmitted via mount contact points 37 shown in FIG. 1 between the focal point control circuit 110 provided in the photographing lens system L and an aperture drive circuit 111.

Said visual axis detecting circuit 101 performs A/D conversion of a signal of an eye ball image from the image sensor 14 (CCD-EYE) and sends the resultant image information to the CPU 100. The CPU extracts respective characteristic points of the eyeball image required for visual axis detection in the way described later, and further calculates the visual axis of the photographer on the basis of positions of respective characteristic points.

Said photometry circuit 102 amplifies a signal from the photometry sensor 10, and then performs logarithmic compression and A/D conversion, and transmits the resultant information as luminance information of respective regions. The photometry sensor 10 consists of four photodiodes for photometry of corresponding four regions in the field of view in a finder shown in FIG. 3: that is, SPC-R for photometry of the left region 210 including the distance measuring points 200 and 201 on the left; CSPC-C for photometry of the center region 211 including the distance measuring point 202; SPC-R for photometry of the right region 212 including the distance measuring points 203 and 204 on the right; and SPC-A for photometry of the marginal region 213 around said three regions.

A line sensor 6f shown in FIG. 5 is a well known CCD line sensor, which consists of five line sensors CCD-L2, CCD-L1, CCD-C, CCD-R1 and CCD-R2 corresponding said five distance measuring points 200 to 204 shown in FIG. 3, respectively.

Said auto focal point detecting circuit 103 performs A/D conversion of voltage applied from said line sensor 6f and sends it to the CPU 100.

A switch SW-1 is closed at the first stroke of the release button 41, thereby starting photometry, auto focal point detection and visual axis detection. A switch SW-2 is a release switch which is closed at the second stroke of the release button. A switch SW-ANG is for the angle detection started by the mercury switch 27 shown in FIG. 1. A switch SW-AEL is a switch which is closed by pushing the AE lock button 43. Switches SW-DIAL 1 and SW-DIAL 2 are dial switches provided in the above-mentioned electronic dial 45 for connecting the electronic dial 45 with the up and down counter of the signal input circuit 104 in order to count the amount of rotation click. Switches SW-M1 to SW-M4 are dial switches provided in the mode dial 44 described above.

Condition signals through these switches are applied to the signal input circuit 104 and sent to the CPU by the data bus.

Said LCD drive circuit comprises well known components for driving the liquid crystal display elements LCDs, and can display a lens opening value, shutter seconds, a selected photographing mode, and so on both in the LCD 42 for monitor and in the LCD 24 in the finder at the same time.

Said LED drive circuit 106 turns on and off the LED for illumination (F-LED) 25 and the LED-21 for superimposition 21.

Said iRED drive circuit 107 selectively turns on the infrared light emitting diodes (IRED 1 to 6) 13a–13f according to conditions.

Said shutter control circuit 108 controls a magnet MG-1 which drives a leading curtain when energized and a magnet MG-2 which drives a trailing curtain when energized so as to expose a photosensitive member to a predetermined amount of light.

Said motor control circuit 109 controls a motor M1 for winding and rewinding the film and a motor M2 for charging the main mirror 2 and the shutters 4.

The above shutter control circuit 108 and the motor control circuit 109 perform a sequence of release operations of the camera.

Figure 6A:
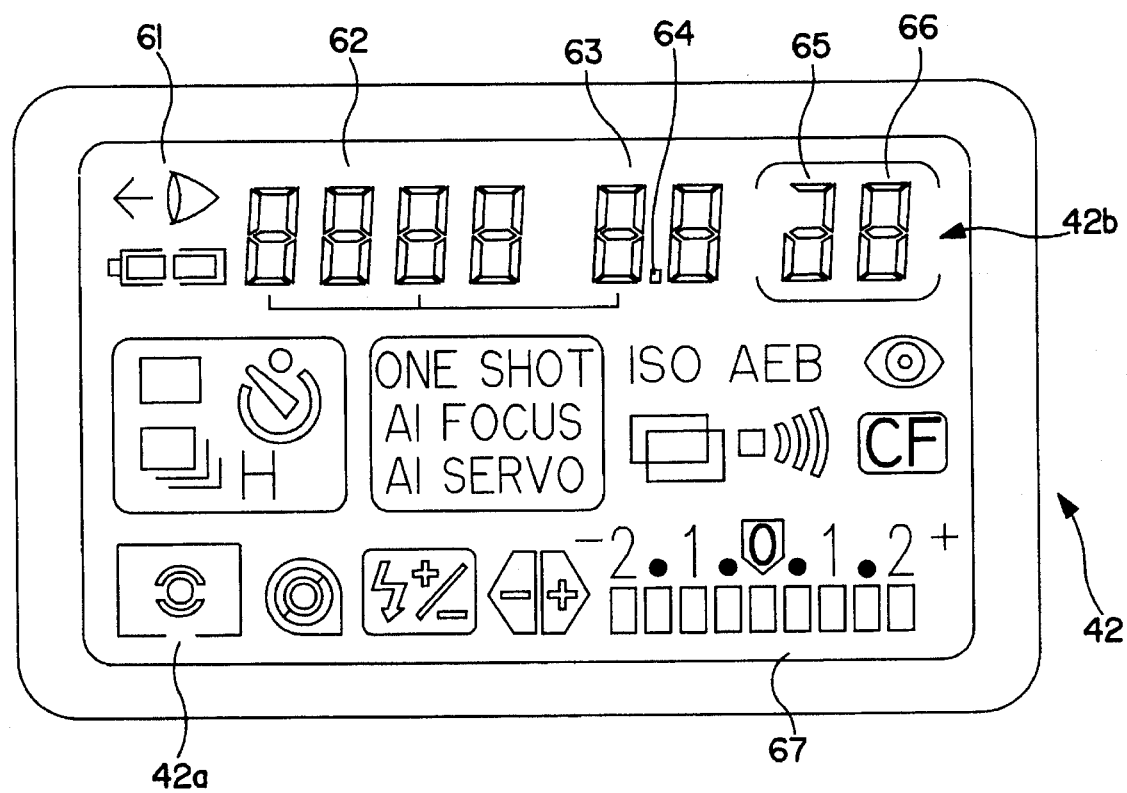
FIGS. 6A and 6B are explanatory views of an LCD for a monitor and an LCD in the finder, respectively.
Figure 6B:
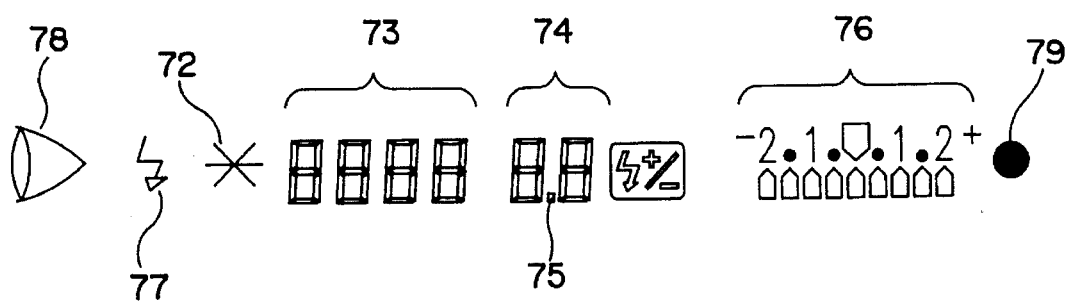
Figure 7:
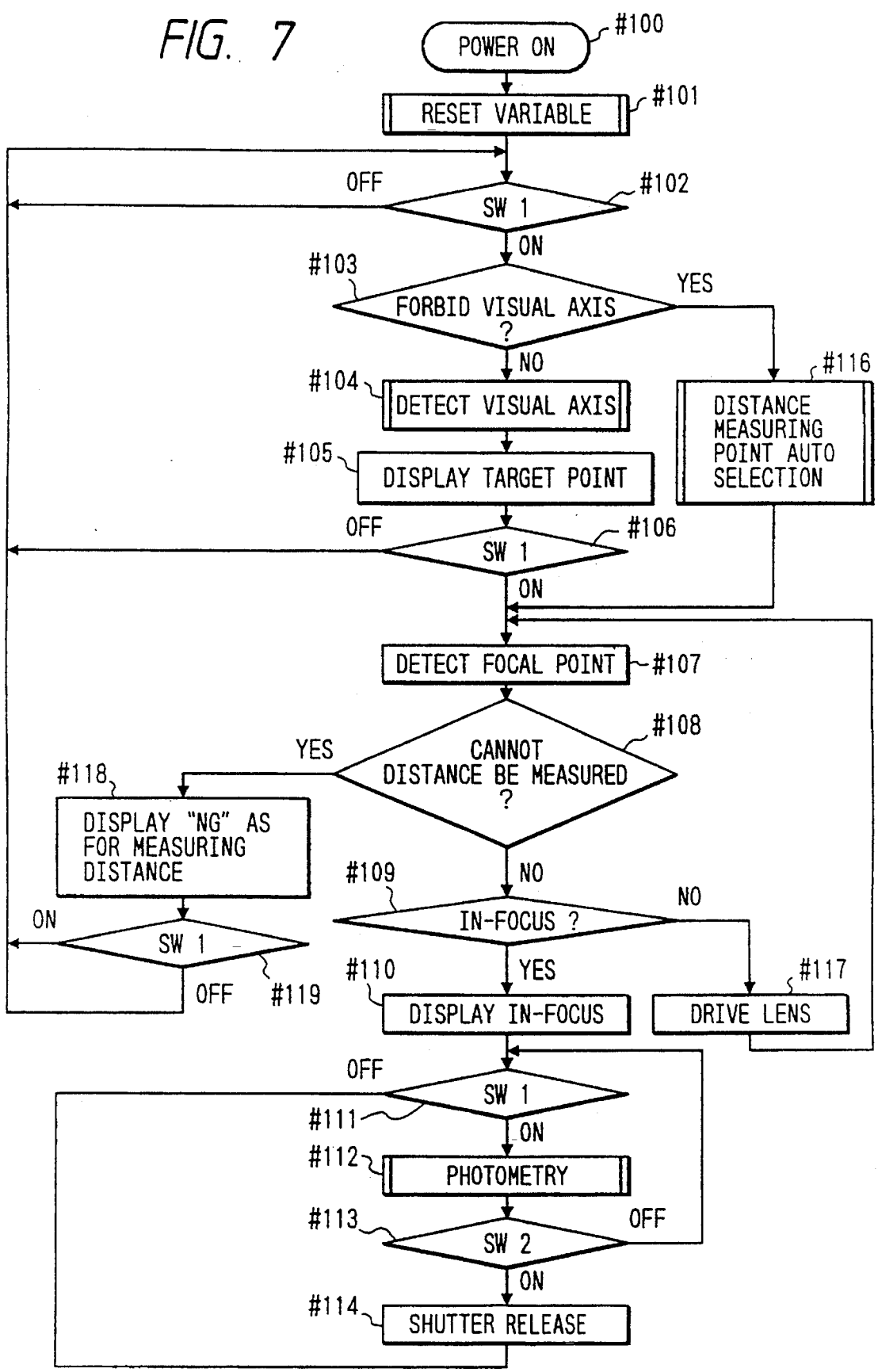
FIG. 7 is a flowchart showing the operation of the single-lens reflex camera shown in FIG. 1.

FIGS. 6A and 6B show all the segments and marks of the LCD 42 for monitor and the LCD 24 in the finder.

In FIG. 6A, the fixed display segment unit 42a has not only typical photographing mode displays but also eye-control input mode display 61 which indicates that the visual axis is detected and that photographing operations such as AF operation, photographing mode selection, and so on are controlled on the basis of the detected visual axis data. Seven-segment unit 42b for displaying variable values consists of: a seven-segment display 62 for displaying shutter seconds of four figures; seven-segments 63 for displaying the lens opening value of two figures; a decimal point display 64; definite value display 65 for displaying the number of films; and a seven-segment display 66 for displaying a number of one figure. Reference numeral 67 denotes exposure correction setting mark. Description of other marks is omitted.

In FIG. 6B, reference numeral 72 denotes an AE lock mark. 73, 74 and 75 denote displays, which are the same as the above-mentioned shutter seconds display and lens opening value displaying. Reference numerals 77, 78 and 79 respectively denote exposure correction setting marks, an eye-control input mark indicating that eye-control input operation is performed, and an in-focus mark indicating that the lens system L is in focus.

Next, operations of the camera having the visual axis detecting mechanism will be described with reference to a flowchart of FIG. 7, and FIGS. 8A to 8C and FIGS. 9A and 9B.

When a certain photographing mode (in the description of this embodiment, the shutter precedence AE mode is exemplified) is set by rotating the mode dial 44, the camera which has been inoperative is energized (step 100) and a variable for visual axis detection which is stored in EEPROM 100a of the CPU 100 is reset (step 101). At the same time, the eye-control input mode display segment 61 and the eye-control input mark 78 are switched on.

At this time, if the mode dial 44 indicates the full auto mode 44d, or if the manual photographing mode in which the lenses are driven manually is switched on by the switch 38 for selecting lens drive operations, the eye-control forbidding mode is set. In the full auto mode 44d, the eye-control input mode display 61 and the eye-control input mark 78 is off. When the manual photographing mode is selected by the switch 38, the eye-control input mark 78 is off (the eye-control input mode display 61 is off), wherein visual axis detection is not performed. That is, in this case, a distance measuring point is selected according to the distance measuring point auto selection subroutine without using the visual axis data (step 116). The auto focal point detecting circuit 103 performs focal point detection operation at the selected distance measuring point (step 107).

As described above, the photographer can optionally select either the eye-control forbidding mode for performing distance measuring point selection without using visual axis data or the eye-control mode for performing distance measuring point selection on the basis of visual axis data.

In this embodiment, as the mode dial 44 is supposed to indicate the shutter precedence AE position, the photographer's visual axis position is calculated according to the visual axis detection subroutine (step 104). Then, the visual axis detected by the visual axis detecting circuit 101 is converted into target point coordinates on the focus plate 7. The CPU 100 selects a distance measuring point close to said target point coordinates and transmits a signal to the LED drive circuit 106 so that the LED 21 for superimposition blinks said distance measuring point mark (step 105). Also, the CPU 100 drives the LCD drive circuit 105 to turn on the eye-control input mark 78 of the LCD 24 in the finder so that the photographer who looks at the region 207, which is outside the field mask 23, in the field of view in a finder can confirm himself that the camera is performing visual axis detection (see FIG. 8A). The seven-segment unit 73 displays the selected shutter seconds (in this embodiment, shutter precedence AE of 1/125 sec. is exemplified).

Figure 8A:
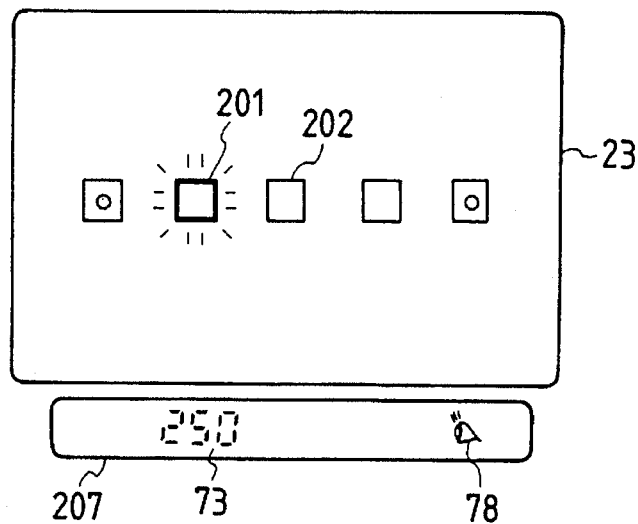
FIGS. 8A, 8B and 8C are views showing display states of the LCD for the monitor and the LCD in the finder, which help understanding of the operation explained in FIG. 7.
Figure 8B:
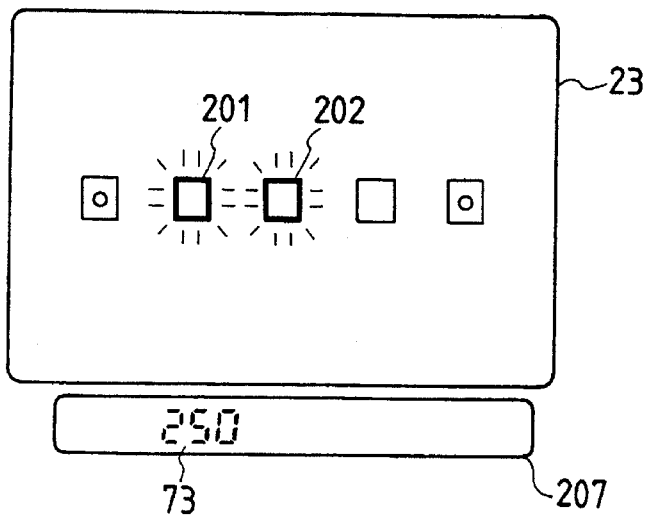
Figure 8C:
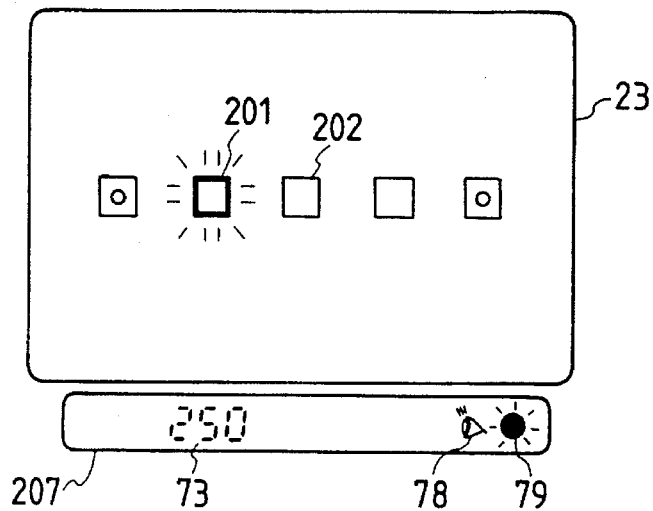

FIGS. 8A and 8C exemplify conditions in which the distance measuring point 201 is selected. In this case, when reliability of the target point coordinates detected by the visual axis detecting circuit 101 is low, eye-control is forbidden (step 116), wherein the eye-control input mark 78 is turned off and distance measuring point automatic selection is executed.

FIG. 8B shows a condition in which reliability of target point detection is lower than the condition of FIG. 8A and the distance measuring point marks 201 and 202 are on.

When the photographer who looks at display indicating the distance measuring point(s) selected according to the visual axis of his own judges it incorrect and lets the release button 41 loose to turn off the switch SW1 (step 106), the camera gets in the standby state, in which the camera remains until the switch SW1 is closed (step 102).

As described above, since the distance measuring point marks in the field of view in a finder blink in order to inform the photographer of the distance measuring point(s) selected according to the visual axis information, the photographer can check whether selection has been done according to his wishes.

When the photographer who looks at display indicating the distance measuring point(s) selected according to the visual axis keeps the switch SW1 on (step 106), the auto-focal point detecting circuit 103 executes focal point detection of at least one distance measuring point according to the detected visual axis data (step 107).

Then, whether the selected distance measuring point is measurable or not is judged (step 108). If not, the CPU 100 sends a signal to the LCD drive circuit 105 in order to blink the in-focus mark 79 of the LCD 24 in the finder, thereby warning the photographer that distance measurement is NG (impossible) (step 118). This warning is continued until the switch SW1 is turned off.

If distance can be measured and the distance measuring point selected according to a predetermined algorithm is out of focus (step 109), the CPU 100 sends a signal to the lens focal point control circuit 110 in order to drive the lens system L by a predetermined amount (step 117). After driving the lenses, the auto-focal point detecting circuit 103 executes focal point detection again (step 107) and judges whether the lens system L is in focus (step 109).

Figure 9A:
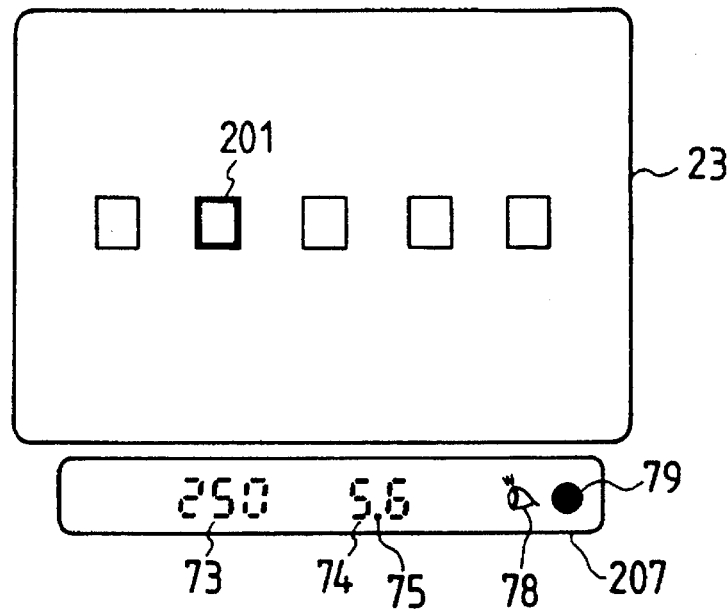
FIGS. 9A and 9B are views showing display states of the LCD for the monitor and the LCD in the finder, which also help understanding of the operation explained in FIG. 7.
Figure 9B:
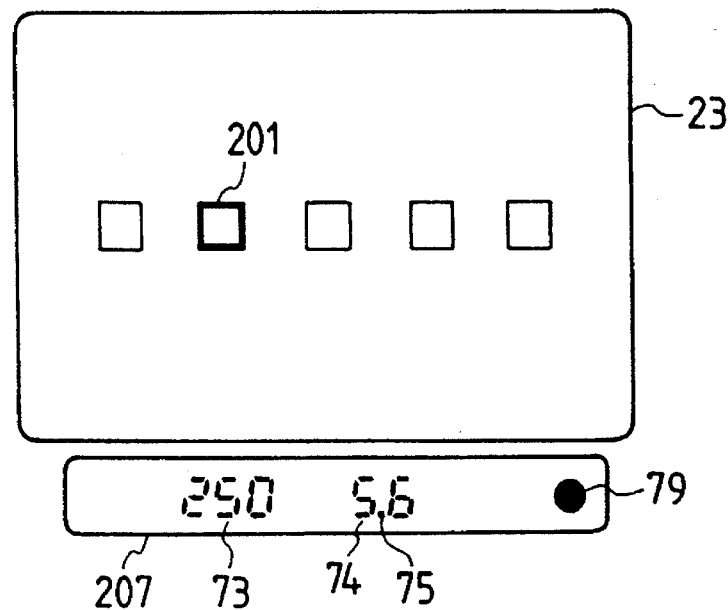

When the photographing lenses L are focalized with respect to the selected distance measuring point, the CPU 100 sends a signal to the LCD drive circuit 105 in order to turn on the in-focus mark 79 of the LCD 24 in the finder, as shown in FIG. 9A. Also, the CPU 100 sends a signal to the LED drive circuit 106 in order to turn on the in-focus mark indicating that the distance measuring point 201 is in focus (step 110).

At this time, the display which indicates the distance measuring point selected on the basis of the visual axis ceases blinking, but is then kept being on in order to inform the photographer that the indicated distance measuring point is brought into focus, which is often the case with focussing operation. For the distance measuring point which is in focus and indicated by the in-focus display usually coincides with the distance measuring point selected on the basis of the visual axis. When the photographer who looks at the display in the finder indicating the distance measuring point in focus judges it incorrect and lets the release button 41 loose to turn off the switch SW1 (step 111), the camera remains in the standby state until the switch SW1 is closed (step 102).

When the photographer who looks at the display indicating the distance measuring point in focus keeps the switch SW1 on (step 111), the CPU 100 sends a signal to the photometry circuit 102 to perform photometry (step 112). At that time, one of photometry region 210 to 213 which includes the distance measuring point in focus is subjected to weighting, and the exposure value is calculated.

In this embodiment, the photometry region 210 which includes the distance measuring point 201 is subjected to weighting, and typical photometry calculation is carried out. The lens opening value (F5.6) obtained from said calculation is displayed by using the seven-segment unit 74 and the decimal point display 75 (see FIG. 9A).

Subsequently, whether the release button 41 is further pushed in to close the switch SW2 or not is judged (step 113). If the switch SW2 is off, the condition of the switch SW1 is checked again (step 111). If the switch SW2 is on, the CPU 100 sends signals to the shutter control circuit 108, the motor control circuit 109 and the aperture drive circuit 111.

More specifically, at first, the motor M2 is energized to lift up the main mirror 2, and the aperture 31 stops down the lenses. Then, the magnet MG1 is energized to open the ante-cover of the shutter 4. The beam limit value of the aperture 31 and the shutter speed of the shutter 4 are determined according to the above-mentioned exposure value detected by the photometry circuit 102 and the sensitivity of the film 5. After a certain lapse of time (that is, the selected shutter speed, which is 1/250 sec.), the magnet MG2 is energized to close the post-cover of the shutter 4. After exposure of the film 5 to light is finished, the motor M2 is energized again to feed the next film frame, when a sequence of shutter release operation is over (step 114). After that, the camera remains in the standby state until the switch SW1 is closed again (step 102).

Now, the "distance measuring point auto-selection" subroutine according to which the operation in said step 116 is performed will be described with reference to FIG. 10.

This subroutine is executed in an eye-control forbidding mode such as the full auto photographing mode and the manual photographing mode, in which distance measuring points are selected without using the visual axis data. In other words, this subroutine is executed when the eye-control input mode is not selected, wherein the distance measuring points are determined on the basis of the defocus amounts of respective distance measuring points and the absolute distance information.

First, whether the five distance measuring points are measurable or not is judged (step 501). When there are no measurable distance measuring points, the operation returns to the main routine (step 511). When only one distance measuring point is measurable (step 502), this distance measuring point is selected (step 507). When two or more distance measuring points are measurable, whether the center distance measuring point is among these measurable points or not is judged (step 503). And when the center distance measuring point is measurable, whether it is within a short distance (for example, twenty times as long as the focal distance of the photographing lenses, or less) or not is judged (step 504).

If the center distance measuring point is both measurable and within a short distance, or if the center distance measuring point is not measurable, the operation proceeds to step 505. In step 505, if more distance measuring points are within a short distance than at long distances, the main object is judged to be remarkably close to the photographer and the nearest distance measuring point is selected (step 506). If more distance measuring points are at long distances than within a short distance, the main object is judged to be at a long distance, the nearest distance measuring points of those at long distances is selected in consideration of the depth of field (step 510).

If the center distance measuring point is judged to be at a long distance in step 504, the operation proceeds to step 508. And if more distance measuring points are at long distances than within a short distance, the main object is judged to be at a long distance, including the distance of the center points, and the center distance measuring point is selected (step 509). If more distance measuring points are within a short distance, the nearest distance measuring point is selected as described before (step 506).

As described above, one measurable distance measuring point is automatically selected if at least one distance measuring point is measurable. And then, the operation returns to the main routine (step 511), and focal point detecting operation is executed again with respect to said selected distance measuring point (step 107).

Incidentally, like the in-focus display (FIG. 9A) in a mode in which the distance measuring point is selected on the basis of the visual axis data, also in this case, not only the in-focus mark 79 but also the display 201 indicating the selected distance measuring point are turned on. In this case, however, the eye-control input mark, of course, is not turned on.

According to the above-mentioned embodiment:

1) Both the eye-control mode in which photographing functions of the camera are controlled on the basis of data of the photographer's visual axis and the eye-control forbidding mode in which said photographing functions of the camera are controlled without using said visual axis data are provided. And when the photographer selects either the full-auto photographing mode or the manual photographing mode the eye-control forbidding mode is uniquely selected; and when the photographer selects other photographing modes, the eye-control mode is uniquely selected. Accordingly, even when visual axis detection is impossible, the photographing functions of the camera can be exhibited without considerable deterioration. And even when a person who has never used the camera before happens to use it on the occasion of, for example, taking a souvenir photo (note that the camera has been learning the visual axis directions of the photographer who frequently uses it, and calculates visual axis data on the basis of said learned visual axis directions), the usability and the photographing functions at least not worse than those of a conventional camera can be realized.

2) A display means for indicating that the photographing functions of the optical apparatus (camera) are controlled according to data of the photographer's visual axis is provided. And, for example, if the eye-control input mark and the auto-focal point detecting means are provided, the distance measuring point selected from a plurality of distance measuring points in the area to be photographed according to the visual axis data is displayed in the finder. Therefore, the photographer can be informed of whether the photographing functions of the camera are controlled according to the visual axis data or not while taking pictures. And when desirable operation cannot be performed on the basis of the visual axis data, for example, when focusing operation is performed manually, the eye-control input mark is turned off. Thus, the photographer is urged to stare at the main object or stop visual axis detection. Accordingly, the visual axis data can be effectively utilized.

As described above, according to the present invention, there are provided: the visual axis detecting means for detecting the rotation angle of the eye ball of the user who looks into the field of view in a finder and detecting the visual axis of the user on the basis of said rotation angle; a control means for controlling the photographing functions according to the visual axis data from said visual axis detecting means in the eye-control mode and controlling the photographing functions without using the visual axis data from said visual axis detecting means in the eye-control forbidding mode; and a selection means for selecting the eye-control mode or the eye-control forbidding mode according to setting of the photographing mode, wherein either said eye-control mode or said eye-control forbidding mode is uniquely selected.

Accordingly, the eye-control mode for performing the photographing operation on the basis of the visual axis data can be restricted, and the eye-control forbidding mode capable of the photographing operation without using said visual axis data can be optionally selected. Therefore, images can be always obtained according to the wishes of the user.

What is claimed is:

1. An apparatus which is controlled according to a plurality of photographing modes relating to exposure control for determining a control mode for a stop value and a shutter speed, said apparatus having predetermined functions and comprising:

visual axis detecting means for detecting directions of a user's visual axis;

control means having an eye-control mode for controlling said functions on the basis of information from said visual axis detecting means, and an eye-control forbidding mode for controlling said functions without using said information from the visual axis detecting means; and selection means for selecting either said eye-control mode or said eye-control forbidding mode according to the selection of a predetermined photographing mode.

2. An apparatus according to claim 1, wherein said predetermined functions include application of distribution of weighting to photometry data.

3. An apparatus according to claim 1, wherein one of said plurality of modes is a full-auto mode, and when this full-auto mode is selected, said selection means selects the eye-control forbidding mode.

4. An apparatus according to claim 1, further comprising display means for executing different display operations corresponding to said eye-control mode and said eye-control forbidding mode, respectively.

5. An apparatus which is controlled according to a plurality of phototaking modes including (i) a phototaking mode for executing an input according to a user's will for a camera control including an exposure control, and (ii) a phototaking mode for being free from the user's will, said apparatus having predetermined functions and comprising:

visual axis detecting means for detecting directions of the user's visual axis;

control means having an eye-control mode for controlling said functions on the basis of information from said visual axis detecting means, and an eye-control forbidding mode for controlling said functions without using the information from said visual axis detecting means; and selection means for selecting either said eye-control mode or said eye-control forbidding mode according to the selection of a predetermined phototaking mode.

6. An apparatus according to claim 5, wherein said predetermined functions include application of distribution of weighting to photometry data.

7. An apparatus according to claim 5, wherein one of said plurality of modes is a full-auto mode, and when this full-auto mode is selected, said selection means selects the eye-control forbidding mode.

8. An apparatus according to claim 5, further comprising display means for executing different display operations corresponding to said eye-control mode and said eye-control forbidding mode, respectively.

9. A photographing apparatus comprising:

visual axis detecting means for detecting a rotation angle of an eyeball of a user who looks into the field of view in a finder and for detecting a visual axis of the user on the basis of said rotation angle;

control means for controlling photographing functions according to the visual axis data from said visual axis detecting means in an eye-control mode and for controlling the photographing functions without using the visual axis data from said visual axis detecting means in an eye-control forbidding mode; and selection means for selecting the eye-control mode or the eye-control forbidding mode according to setting of a photographing mode, wherein said selection means singularly selects either the eye-control mode or the eye-control forbidding mode according to the selected photographing mode, wherein selection by said selection means depends upon whether a predetermined photographing mode or another photographing mode is selected from a plurality of photographing modes provided, and wherein the predetermined photographing mode is a full-auto photographing mode in which all the photographing functions are automatically selected.

10. A photographing apparatus according to claim 9, further comprising eye-control mode display means for performing different display operations corresponding to said eye-control mode and said eye-control forbidding mode, respectively.

11. An apparatus which is controlled according to a plurality of operation modes, said apparatus having predetermined functions and comprising:

visual axis detecting means for detecting directions of a user's visual axis;

control means having an eye-control mode for controlling said functions on the basis of information from said visual axis detecting means, and an eye-control forbidding mode for controlling said functions without using said information from said visual axis detecting means;

selection means for selecting either said eye-control mode or said eye-control forbidding mode according to the selection of said operation modes; and display means for executing different display operations corresponding to said eye-control mode and said eye-control forbidding mode, respectively.

12. An apparatus according to claim 11, wherein a display when said eye-control mode is executed is a symbol for expressing an eye.

13. An image-taking apparatus provided with a plurality of image-taking modes, comprising:

visual axis detection means for detecting a visual axis;

selecting means for selecting any mode of the plurality of image-taking modes; and controlling means for controlling function of said image-taking apparatus based on visual axis detection by said visual axis detection means or for controlling function of said image-taking apparatus not based on the visual axis detection, in accordance with the selected mode.

14. An apparatus according to claim 13, wherein said controlling means performs control for exposure for said image-taking apparatus.

15. An apparatus according to claim 13, wherein said controlling means performs control for focusing for said image-taking apparatus.

16. An apparatus according to claim 13, wherein said controlling means performs control for exposure and focusing for said image-taking apparatus.

17. An apparatus according to claim 13, further comprising displaying means for displaying a mark relating to the visual axis when control based on the visual axis detection is performed.

18. An apparatus according to claim 17, wherein the mark comprises a mark relating to an eye.

19. An apparatus according to claim 18, wherein the mark comprises a symbol for indicating an eye.

20. An apparatus according to claim 13, wherein said controlling means controls function of said image-taking apparatus not based on the visual axis detection when an automatic mode is selected by said selecting means.

21. An apparatus according to claim 20, wherein said controlling means controls said image-taking apparatus without performing the visual axis detection when the automatic mode is selected by said selecting means.

22. An image-taking apparatus provided with a plurality of image-taking modes, comprising:

visual axis detection means for detecting a visual axis;

selecting means for selecting any mode of the plurality of image-taking modes, wherein the plurality of image-taking modes include an automatic mode and a non-automatic mode; and controlling means for controlling function of said image-taking apparatus based on visual axis detection by said visual axis detection means when the non-automatic mode is selected and for controlling function of said image-taking apparatus not based on the visual axis detection when the automatic mode is selected.

23. An apparatus according to claim 22, wherein said controlling means performs controlling exposure for said image-taking apparatus.

24. An apparatus according to claim 22, wherein said controlling means performs controlling focusing for said image-taking apparatus.

25. An apparatus according to claim 22, wherein said controlling means performs controlling exposure and focusing for said image-taking apparatus.

26. An apparatus according to claim 22, further comprising displaying means for displaying a mark relating to the visual axis when controlling based on the visual axis detection is performed.

27. An apparatus according to claim 26, wherein the mark comprises a mark relating to an eye.

28. An apparatus according to claim 27, wherein the mark comprises a symbol for indicating an eye.

29. An apparatus according to claim 22, wherein said controlling means controls function of said image-taking apparatus not based on the visual axis detection when the automatic mode is selected by said selecting means.

* * * * *